United States Patent
Tourek et al.

(10) Patent No.: US 6,607,754 B1
(45) Date of Patent: Aug. 19, 2003

(54) **DELIVERY OF *HYPERICUM PERFORATUM* (ST. JOHN'S WORT) IN TABLET FORM**

(75) Inventors: William J. Tourek, Plymouth, MN (US); Samuel Daisy, Jr., Minneapolis, MN (US)

(73) Assignee: Upsher-Smith Laboratories, Inc., Minneapolis, MN (US)

(*) Notice: Subject to any disclaimer, the term of this patent is extended or adjusted under 35 U.S.C. 154(b) by 903 days.

(21) Appl. No.: 08/890,705

(22) Filed: Jul. 11, 1997

(51) Int. Cl.$^7$ ............................ A01N 65/00; A61K 9/28
(52) U.S. Cl. ...................... 424/730; 424/451; 424/452; 424/463; 424/464; 424/725; 514/960
(58) Field of Search .............................. 424/195.1, 451, 424/452, 457, 463, 464, 730, 725; 514/960

(56) References Cited

U.S. PATENT DOCUMENTS

| | | | | |
|---|---|---|---|---|
| 4,898,891 A | * | 2/1990 | Lavie et al. ................. | 514/732 |
| 5,126,145 A | * | 6/1992 | Evenstad et al. ............ | 424/465 |
| 5,288,485 A | * | 2/1994 | Kikuta et al. ................. | 424/74 |

FOREIGN PATENT DOCUMENTS

| | | |
|---|---|---|
| EP | 0256454 | 2/1988 |
| EP | 0702957 | 3/1996 |
| EP | 0847756 | 6/1998 |
| WO | 89/09056 | 10/1989 |
| WO | 97/13489 | 4/1997 |
| WO | 97/22354 | 6/1997 |

OTHER PUBLICATIONS

The National Gardening Association Dictionary Of Horticulture, The Philip Lief Group, Inc., Penguin Books, NY, NY pp. 230–231, 1996.*

Remington's Pharmaceutical Sciences, 16th Edition, Mack Publishing Co., Easton, PA, pp. 1553–1566, 1980.*

"Oral Solid Dosage Forms", *In: Remington's Pharmaceutical Sciences*, Chapter 90, 17th Edition, A.R. Gennaro et al., eds., Mack Publishing Co., Easton, PA, 1610–1614, (1985).

Lachman, L., et al., "Tablets", *In: The Theory and Practice of Industrial Pharmacy*, 3rd Edition, Lea & Febiger, Philadelphia, PA, 318–320, (1986).

Miller, S., "A Natural Mood Booster", *Newsweek*, 74–75, (May 5, 1997).

Tyler, V.E., "The Herbal Remedies Market, St. John's Wort", *Chemtech*, 56–57, (May 1997).

* cited by examiner

*Primary Examiner*—Brenda Brumback
(74) *Attorney, Agent, or Firm*—Schwegman, Lundberg, Woessner & Kluth, P.A.

(57) ABSTRACT

St. John's Wort has been indicated as a beneficial supplement to human diet. It has been traditionally provided as an extract, tincture, tea or capsule form, usually administered in amounts taken three times/day. It has been found that the manufacture of a tablet of this supplement material is a complex process, and that St. John's Wort extract is not amenable to wet tableting. A tablet which can be taken twice a day to provide a recommended supplemental level of St. John's Wort is described as comprising by weight of the tablet:

- 400 to 500 mg St. John's Wort extract as 57 to 75% by weight of the tablet,
- 1.0–5.0% by weight binder,
- 8–18% by weight dissolution regulator,
- up to 30% by weight filler,
- 0.2 to 5.0% by weight glidant, and
- 0.5 to 2.5% by weight lubricant/glidant.

A process for manufacturing the tablet comprises the steps of a) mixing components comprising:
  - 400 to 500 mg St. John's Wort extract as 57 to 75% by weight of the tablet,
  - 1.0–5.0% by weight binder,
  - 8–18% by weight dissolution regulator,
  - up to 30% by weight filler,
  - and less than a final proportion of glidant and lubricant/glidant of 0.2 to 5.0% by weight glidant, and 0.5 to 2.5% by weight lubricant/glidant to form a slug, b) breaking the slug down into particulates which can be subsequently compressed into a tablet, c) adding sufficient glidant and/or lubricant glidant to form a composition with proportions of glidant and lubricant/glidant of 0.2 to 5.0% by weight glidant, and 0.5 to 2.5% by weight lubricant/glidant, and d) compressing the composition to form a tablet.

17 Claims, No Drawings

DELIVERY OF *HYPERICUM PERFORATUM* (ST. JOHN'S WORT) IN TABLET FORM

BACKGROUND OF THE INVENTION

1. Field of the Invention

The present invention relates to the delivery of St. John's Wort (*Hypericum perforatum*, active ingredient hypericin) in tablet form in increased dosimetric volumes at decreased frequency of administration.

2. Background of the Art

The use of naturally occurring organic materials for dietary supplements as well as for specific medical treatments has increased dramatically over the past decades. Significant medical treatments have resulted from investigation of herblore and folklore treatment with common plants. Commercially, the plants have been treated for consumption and provided in powder or tablet format for the public. As with conventional delivery of medicines, the supplements must be delivered in sufficient quantity to have their desired effect, have the delivery spread out over the course of the day rather than spiked at a single intake (especially if the supplement can not be stored by the body), and yet have the likelihood of compliance by the patient with the recommended dosage. These requirements may often be in conflict with each other, with increased frequency of delivery competing against the likelihood of dosage compliance by the patient, for example.

Not all supplements are compatible with some of the drug delivery means available to provide effective administration of the drugs or supplements. For example, some materials cannot be delivered transcutaneously because of their molecular size or oleophilicity, some materials cannot be effectively administered orally, some drugs are not stable in tablet form, and therefore each supplement or drug must be considered independently.

BRIEF DESCRIPTION OF THE INVENTION

The active ingredient of St. John's Wort (*Hypericum perforatum*, hypericin) has been found to be deliverable by tablet format in administered levels sufficient to allow b.i.d. (twice a day) supplements to a person. The size of a full tablet is within patient acceptable size range, and the use of timed release ingredients within the tablet allow for the b.i.d. supplement to provide acceptable levels of the hypericin over the course of the day. This increases the likelihood of compliance with daily administration levels without the person attempting to catch up to supplement requirements with a double administration.

DETAILED DESCRIPTION OF THE INVENTION

St. John's Wort has been reported in the literature (Newsweek, May 5, 1997; Chemtech, 56 May 1997) to provide relief from inflammation, promote healing and, more recently, as an antidepressant. It has been administered as a tea, a tincture, a purified extract, and a capsule. The optimum administration level is reported to be 300 mg of Hypericum extract (containing about 0.3% by weight of the active ingredient, hypericin), taken three times a day (t.i.d.). As with any delivered treatment, the more often delivery is required, the lower the rate of administration compliance by the person. Particularly with a three times a day requirement, at least one of these administration is likely to have to occur away from the home, where the compliance rate is the lowest. It has been reported (ibid, Newsweek) that some patients have tolerated 500 mg St. John's Wort in liquid dosage three times per day.

The present invention describes the use of tablets comprising from 400 to 500 mg of Hypericum extract with 0.2 to 0.4 % of the active ingredient in tablet form. The St. John's Wort extract comprises from about 40 to 75% by weight with smaller dose (less than 450 mg) tablets and 57 to 75% by weight of the tablet with the larger dose of greater than 450 mg. In a controlled release tablet form, this large dose is administered with more of the appearance of a larger number of smaller doses.

A general composition would comprise a tablet comprising 400 to 500 mg (57 to 75% by weight solids in the tablet) of Hypericum extract (representing about 0.3% by weight of the active ingredient, hypericin), 8–20% by weight of the tablet of dissolution regulator, 1.5 to 4% by weight binder, 0% or preferably 10 to 20% by weight optional filler, 0.2 to 5.0% by weight glidant, and 0.2 to 2.5% by weight lubricant/glidant.

The controlled release tablet includes the St. John's Wort supplement and a hydrophilic polymer matrix for achieving controlled or sustained or extended release of the supplement. The tablet can include a high proportion of the supplement and cannot easily be prepared by standard wet granulation techniques. A desirable dissolution profile can be achieved. The tablet can be scored to permit easy titration up to the desired supplement level.

The supplement can be any suitable therapeutically active material comprising the Hypericum extract with active amounts of hypericin, which is commonly administered orally. The solubility of the supplements could range from about 0.1 to 30% (at 25° C.). This includes slightly soluble to freely soluble compounds, according to the definitions provided by Remington Pharmaceutical Sciences.

The minimum amount of supplement or active hypericin extract in the tablets of the invention will typically be at least about 45% for small dose tablets and 57% by weight for larger dose tablets based on the weight of the tablet and can range up to about 75%. A narrow preferred range would be from 62 to 70% by weight of the total tablet of the hypericum extract (with from 0.10 to 0.6% by weight active ingredient, more preferably 0.15 to 0.5%, most preferably 0.15 to 0.4%).

The hydrophilic polymer matrix of the tablets of the invention is a dynamic system involving hydroxypropyl methylcellulose wetting, hydration, and dissolution. Other soluble excipients or drugs also wet, dissolve, and diffuse out of the matrix while insoluble materials are held in place until the surrounding polymer/excipient/drug complex erodes or dissolves away.

The most significant mechanism by which drug release is controlled is through the use of hydroxypropyl methylcellulose. The hydroxypropyl methylcellulose, present throughout the tablet, partially hydrates on the tablet surface to form a gel layer. Overall dissolution rate and supplement availability are dependent on the rate of soluble supplement diffusion through the wet gel and the rate of tablet erosion. Hydroxypropyl methylcellulose with substitution rates of about 7–30% for the methoxyl group and greater than 7% or about 7–20% for the hydroxypropoxyl group are preferred for formation of this gel layer. More preferred are substitution rates of 19–30% for the methoxyl group and 7–12% for the hydroxypropyl group.

Hydroxypropyl methylcelluloses vary in their viscosity, methoxy content, and hydroxypropoxyl content. Properties also vary. Some have more sustaining properties or the ability to achieve controlled release of supplements. Others have good binding properties and are less desirable for sustained properties. By "binding properties" we are referring to the ability to act as a binding agent for tablet production by wet granulation, for example, incorporating the hydroxypropyl methylcellulose into aqueous solution in order to spray onto the dry powders. Hydroxypropyl methylcelluloses with good sustaining properties are too viscous for use as the binder in wet granulation techniques.

The tablets of the invention comprise about 5–30 percent by weight hydroxypropyl methylcellulose with sustaining properties and only slight binding properties. Such hydroxypropyl methylcelluloses generally have a viscosity of no less than about 1000 centipoise.

More typically, the viscosity will be no less than about 4000 cps. For improved performance, the tablet will comprise about 8–20 weight percent, or, more preferably, about 10–15 percent hydroxypropyl methylcellulose with sustaining characteristics, as represented by METHOCEL K100.

A preferred hydroxypropyl methylcellulose with sustaining properties is a hydroxypropyl methylcellulose with substitution type 2208, with a nominal viscosity, 2% aqueous, of about 100,000 cps, a methoxyl content of about 19–24%, and a hydroxypropoxyl content of about 7–12%. A "controlled release" grade is preferred, with a particle size where at least 90% passes through a #100 USS mesh screen. A commercially available hydroxypropyl methylcellulose meeting these specifications is METHOCEL K100MCR from The Dow Chemical Company.

The tablet further comprises or includes about 1–5 weight percent water-soluble pharmaceutical binder. The binder or binding agent aids in tablet production by granulation, serving as an adhesive and adding strength to the tablet.

Many suitable binders are known. They include polyvinyl pyrollidone, starch, gelatin, sucrose, lactose, methylcellulose, hydroxypropyl methylcellulose, and the like. For good binding action without excess binding agent, we prefer the use of about 1.5–4% by weight, or more preferably, particularly where the preferred binding agent is used, about 2–3% by weight.

The preferred water-soluble pharmaceutical binder for use in this invention is hydroxypropyl methylcellulose having binding properties. Such hydroxypropyl methylcelluloses typically have a much lower viscosity than the hydroxypropyl methylcelluloses that have good sustaining characteristics. Generally, the viscosity of a 2% aqueous solution will be less than about 1000 cps. More typically, it will be less than 100 cps.

A preferred hydroxypropyl methylcellulose for use as a binding agent in the context of the invention has a nominal viscosity, 2% aqueous, of about 15 cps, a methoxy content of about 28–30%, a hydroxypropyl content of about 7–12%, and a particle size of 100% through USS 30 mesh screen and 99% through USS 40 mesh screen. Hydroxypropyl methylcellulose 2910, METHOCEL E15 from The Dow Chemical Company, meets these standards and is a preferred binder.

Other suitable binding hydroxypropyl methylcelluloses include, METHOCEL E5LVP, METHOCEL E5OLVP, and METHOCEL K3P. The methylcellulose METHOCEL A15LVP can also be used.

Another binder we recommend is polyvinyl pyrollidone, also known as polyvidone, povidone, and PVP. Typical properties of commercially available PVP's include density between 1.17 and 1.18 g/ml and an average molecular weight ranging from about 10,000 to 360,000. Generally, the higher molecular weight PVP's would be more suitable for use in this invention. Suppliers include BASF Wyandotte and GAF.

An optional component of the invention is what is referred to as a hydrophobic component. This component ordinarily permits granulation of soluble medicaments with hydroxypropyl methylcellulose where it would not otherwise be easily accomplished using standard wet granulation techniques.

The hydrophobic component may comprise a wax-like material, but as a less preferred material. The wax-like material comprises a solid generally insoluble substance having a waxy consistency. It should, of course, be ingestible. Many such materials are known and include waxes such as beeswax, carnauba wax, candelilla wax, Japan wax, paraffin, hydrogenated castor oil, higher fatty acids, such as palmitic acid, stearic acid, and myristic acid, esters of such higher fatty acids such as substituted mono-, di- and triglycerides, acetylated monoglycerides, glyceryl monostearate, glyceryl behenate, glyceryl tristearate, cetyl palmitate, glycol stearate, glyceryl tri-myristate, higher fatty alcohols such as cetyl alcohol, stearyl alcohol, and myristyl alcohol, and mixtures thereof.

Two wax-like materials are preferred in view of their ready availability in powdered form, reasonable cost, ease of handling, and their effectiveness in the context of this invention. These waxy materials are hydrogenated vegetable oil and stearic acid. Hydrogenated vegetable oil generally consists mainly of the triglycerides of stearic and palmitic acids, and is readily commercially available. A referred hydrogenated vegetable oil for use in this invention is available through Edward Mendell Co., Inc. of N.Y. under the trademark LUBRITAB®. The LUBRITAB® product has a bulk density of 0.48–0.56 grams per milliliter, a melting point of from 61°–66° C., a saponification value of 188–198, 0.8 maximum unsaponifiable matter, and a typical particle size distribution of 15 percent maximum on 100 mesh USS screen, 35 percent maximum through 200 mesh USS screen. An advantage of this product is its availability in powder form. Equivalent preferred products include Kalshamns STEROTEX with a melting point of 61–66° C., a saponification value of 188–198, 0.8 maximum unsaponifiable matter, and a typical particle size distribution of 5 percent maximum on 100 mesh USS screen, and 1 percent maximum through 40 mesh USS screen. A similar hydrogenated vegetable oil is available from Durkee, under the trademark DURATEX™.

Stearic or octadecanoic acid is typically manufactured from fats and oils derived from edible sources, and commercial stearic acid is typically a mixture of stearic acid ($C_{18}H_{36}O_2$) and palmitic acid ($C_{16}H_{32}O_2$). Stearic acid is available from many chemical suppliers, including Emery Industries and Mallinckrodt, Inc.

The powdered stearic acid NF available from Mallinckrodt contains not less than 40.0 percent $C_{18}H_{36}O_2$ and not less than 40.0 percent $C_{16}H_{32}O_2$, the sum of these two components is not less than 90.0 percent. The congealing temperature is not lower than 54°, and the iodine value is not more than 4.

The hydrophobic component, if present, would be used in an amount effective to permit granulation of the controlled release tablet. Such an amount is commonly 2–20 percent by weight of the tablet depending on the solubility of the supplement. Higher concentrations will be required for more soluble supplements. Preferably, for good granulating results and sustained release, it will be present at from 5–15 percent of the total tablet weight, or more preferably, 6–12 percent by weight.

Other components commonly used in tablet formation, such as external lubricants, dyes, fillers and extenders, may also be used as desired. External lubricants or tableting aids can include calcium stearate, stearic acid, hydrogenated vegetable oils, talc, corn starch, colloidal silicone dioxide, magnesium stearate, and glyceryl behenate.

The external lubricants, typically added to the dried granules before tableting, if used, can be present at up to about 5 percent of the total tablet weight. More preferably, they will be present at 0.2–0.8 percent, or for improved tableting, 0.5–3 percent of the tablet weight.

It is preferred that a coating be applied to the tablet after final tableting. The St. John's Wort composition is quite unattractive, being nearly black, so a colored coating is preferred. The coating may be of sugar or soluble or digestible polymer (e.g., hydroxypropylmethylcellulose) to mask the rather bitter taste of the supplement.

Fillers or extenders can be used if needed or desired. When a tablet containing a 450 mg dose of St. John's Wort extract is formed, fillers or extenders typically would not be used in large quantities, because the supplement itself supplies sufficient volume to the tablet. However, fillers or extenders may be desirable where a lower dose of supplement is used. Many fillers or extenders are known and are readily available, including calcium sulfate, dicalcium phosphate, tricalcium phosphate, lactose, sucrose, starch dextrose, and microcrystalline cellulose. Fillers may comprise up to 20 or 30% by weight of the tablet, and are preferably inorganic oxides and hydrates thereof such as dibasic calcium phosphate dihydrate.

The methods of forming the tablets of the invention generally excludes the typical wet granulation methods, either conventional or fluid bed. The nature of the supplement is such that conventional processing by wet compression or wet granulation did not work for reasons not previously known to the inventors. Initial efforts at wet granulation produced a tar-like product. Replacement of the water base with solvents (isopropyl alcohol and water) improved the consistency somewhat, but control of the composition was still difficult. There was the potential with the use of solvents that the organic solvents would degrade the active materials of the supplement, so that conventional alternative did not appear to be viable. Only with actual manual control of the delivery of the solvent based system was tableting reasonably effective, but was clearly more costly because of the level of personnel control and the use of higher cost (compared to water) solvents. It was next attempted to form the tablets by planetary mixing, with ingredients mixed in a batch, and compressed to tablet form. This was somewhat more successful, but again tended to require manual operation for consistency. These types of processing were particularly unsuitable for St. John's Wort because, at least in part because it is a natural product, its consistency can vary quite significantly from lot to lot. It has proven to be incompatable or extremely difficult to perform with each of these types of tableting.

The following process, a form of dry granulation, compression granulation or slugging, as it is variously referred to in the art, had to be designed to enable the supplement materials to be tableted with consistency. This process is inventive for any dose level of St. John's Wort in tablet form, and is not to be limited to the use level of the tablet of the invention (e.g., 450 or 500, etc. mg. of St. John's Wort extract). Ingredients comprising the St. John's Wort extract, binder, dissolution regulator, glidant and lubricant glidant (in amounts of glidant and/or lubricant glidant less than that intended for the final product) are first blended into a first composition and compressed into a pre-tablet or slug. The slug is ground (and usually screened), the remaining glidant and/or lubricant from: the final formulation added to form a second composition, and then the second composition is compressed into a tablet. This type of process has previously been used where the components of the tablet are sensitive to moisture (as by degradation) or are unable to withstand the elevated temperatures of drying. The components of the present tablet are neither degraded by moisture nor sensitive to drying temperatures, so dry granulation was not a natural method selected for the tableting of the St. John's Wort supplement. Rather, many factors, including a hygroscopic effect, led to the necessity of a dry process based upon the repeated efforts of the inventors. In addition to these aspects of the process, the open environment wherein mixing, tableting, grinding and compressing are performed should be kept at relative humidity below 50%, preferably below 45%, and more preferably below 40% to avoid absorption of moisture by the hygroscopic material, which adversely affects the physical properties of the materials during processing and necessitates greater controls and introduces more difficulty into the procedures for tableting the supplement.

A general range of materials would comprise:
  400 to 500 mg St. John's Wort extract as 57 to 75% by weight of the tablet,
  1.0–5.0% binder,
  8–18% by weight dissolution regulator,
  up to 30% by weight filler,
  0.2 to 5.0% glidant, and
  0.5 to 2.5% lubricant glidant The method of manufacturing the tablets according to the improved process of the present invention comprises a method for manufacturing by dry granulating a tablet for the delivery of the active ingredient of St. John's Wort, said tablet comprising by weight of the tablet:
  400 to 500 mg St. John's Wort extract as 57 to 75% by weight of the tablet,
  1.0–5.0% by weight binder,
  8–18% by weight dissolution regulator,
  up to 20% by weight filler,
  0.2 to 5.0% by weight glidant, and
  0.5 to 2.5% by weight lubricant/glidant said method comprising the steps of
    a) mixing components comprising:
      400 to 500 mg St. John's Wort extract as 57 to 75% by weight of the tablet,
      1.0–5.0% by weight binder,
      8–18% by weight dissolution regulator,
      up to 20% by weight filler,
      and less than a final proportion of glidant and lubricant/glidant of 0.2 to 5.0% by weight glidant, and 0.5 to 2.5% by weight lubricant/glidant to form a slug,
    b) breaking the slug down into particulates which can be subsequently compressed into a tablet,
    c) adding sufficient glidant and/or lubricant glidant to form a composition with proportions of glidant and lubricant/glidant of 0.2 to 5.0% by weight glidant, and 0.5 to 2.5% by weight lubricant/glidant, and
    d) compressing the composition to form a tablet.

A specific tablet formulation for the administration of St. John's Wort is shown in the following table.

| Mg/TABLET | PERCENT | PURPOSE | INGREDIENTS |
|---|---|---|---|
| 450.00 | 64.0 | ACTIVE | St. John's Wort Extract |
| 98.44 | 14.0 | Dissolution Regulator | Hydroxypropyl Methylcellulose 2208 (Methocel K100) |
| 105.47 | 15.0 | Filler | Dibasic Calcium Phosphate Dihydrate |
| 21.09 | 3.0 | Glidant | Silicon Dioxide (Syloid 244) |
| 10.55 | 1.5 | Lubricant/Glidant | Magnesium Stearate |
| 17.58 | 2.5 | Binder | Hydroxypropyl Methylcellulose 2910 (Methocel E15LV) |
| 703.13 | 100.0 | TOTAL | |

What is claimed is:

1. A method for manufacturing by dry granulation a tablet for the delivery of the active ingredient of St. John's Wort, said tablet comprising by weight of the tablet:
   40 to 75% by weight St. John's Wort extract,
   1.0–5.0% by weight binder,
   8–18% by weight dissolution regulator,
   up to 30% by weight filler,
   0.2 to 5.0% by weight glidant as a final proportion of glidant, and
   0.5 to 2.5% by weight lubricant as a final proportion of lubricant; said method comprising the steps of:
   a) mixing components comprising:
      40 to 75% by weight St. John's Wort extract,
      1.0–5.0% by weight binder,
      8–18% by weight dissolution regulator,
      up to 30% by weight filler,
      and less than at least one of the final proportion of glidant and the final proportion of lubricant of 0.2 to 5.0% by weight glidant, and 0.5 to 2.5% by weight lubricant to form a slug,
   b) breaking the slug down into particulates which can be subsequently compressed into a tablet,
   c) adding sufficient glidant and/or lubricant to form a composition with final proportions of both glidant and lubricant of 0.2 to 5.0% by weight glidant, and 0.5 to 2.5% by weight lubricant, and
   d) compressing the composition to form a tablet.

2. The method of claim 1 wherein said St. John's Wort extract is present as 400 to 500 mg per tablet and 57 to 75% by weight of the tablet.

3. The method of claim 2 wherein a digestibly acceptable coating is applied to the tablet.

4. The method of claim 3 wherein said coating comprises a coating material selected from the group consisting of sugar and cellulose polymers.

5. The method of claim 3 wherein said coating comprises hydroxypropylmethylcellulose.

6. The method of claim 1 wherein less than the final proportion of glidant is added in step a) and glidant is added in step c) to form a composition with proportions at the final proportion for glidant.

7. The method of claim 1 wherein less than the final proportion of glidant and lubricant is added in step a) and glidant and lubricant are added in step c) to form a composition with proportions of the final proportion for glidant and lubricant.

8. The method of claim 3 wherein less than the final proportion of glidant is added in step a) and glidant is added in step c) to form a composition with proportions at the final proportion for glidant.

9. The method of claim 3 wherein less than the final proportion of glidant and lubricant is added in step a) and glidant and lubricant are added in step c) to form a composition with proportions of the final proportion for glidant and lubricant.

10. The method of claim 4 wherein less than the final proportion of glidant is added in step a) and glidant is added in step c) to form a composition with proportions at the final proportion for glidant.

11. The method of claim 4 wherein less than the final proportion of glidant and lubricant is added in step a) and glidant and lubricant are added in step c) to form a composition with proportions of the final proportion for glidant and lubricant.

12. The method of claim 1 wherein the dissolution regulator comprises hydroxyprocpyl methylcellulose in an amount of from 8–18% by weight of said components of step a).

13. The method of claim 3 wherein the dissolution regulator comprises hydroxypropyl methylcellulose in an amount of from 8–18% by weight of said components of step a).

14. The method of claim 4 wherein the dissolution regulator comprises hydroxypropyl methylcellulose with substitution rates of between 7 and 30% for methoxy groups and 7–20% for hydroxypropyl groups in an amount of from 8–18% by weight of said components of step a).

15. The method of claim 5 wherein the dissolution regulator comprises hydroxypropyl methylcellulose with substitution rates of between 7 and 30% for methoxy groups and 7–20% for hydroxypropyl groups in an amount of from $8 \geq 18\%$ by weight of said components of step a).

16. The method of claim 6 wherein the dissolution regulator comprises hydroxypropyl methylcellulose with substitution rates of between 7 and 30% for methoxy groups and 7–20% for hydroxypropyl groups in an amount of from 8–18% by weight of said components of step a).

17. The method of claim 7 wherein the dissolution regulator comprises hydroxypropyl methylcellulose with substitution rates of between 7 and 30% for methoxy groups and 7–20% for hydroxypropyl groups in an amount of from 8–18% by weight of said components of step a).

* * * * *